United States Patent
Gao et al.

(10) Patent No.: US 11,208,427 B2
(45) Date of Patent: Dec. 28, 2021

(54) DICAFFEOYL SPERMIDINE DERIVATIVE GLYCOSIDES AND USE THEREOF

(71) Applicant: Jinan University, Guangdong (CN)

(72) Inventors: Hao Gao, Guangdong (CN); Xinsheng Yao, Guangdong (CN); Rongrong He, Guangdong (CN); Guodong Chen, Guangdong (CN); Zhengqun Zhou, Guangdong (CN); Chuanxi Wang, Guangdong (CN); Dan Hu, Guangdong (CN); Hongxia Fan, Guangdong (CN)

(73) Assignee: Jinan University, Guangdong (CN)

( * ) Notice: Subject to any disclaimer, the term of this patent is extended or adjusted under 35 U.S.C. 154(b) by 0 days.

(21) Appl. No.: 16/070,607

(22) PCT Filed: Jan. 13, 2017

(86) PCT No.: PCT/CN2017/071119
§ 371 (c)(1),
(2) Date: Jul. 17, 2018

(87) PCT Pub. No.: WO2017/124970
PCT Pub. Date: Jul. 27, 2017

(65) Prior Publication Data
US 2019/0292212 A1  Sep. 26, 2019

(30) Foreign Application Priority Data
Jan. 19, 2016  (CN) .......................... 201610032769.0

(51) Int. Cl.
| A61P 25/28 | (2006.01) |
| A61P 31/14 | (2006.01) |
| A61P 25/16 | (2006.01) |
| A61K 31/165 | (2006.01) |
| A61P 25/14 | (2006.01) |
| A61P 25/00 | (2006.01) |
| C07H 15/203 | (2006.01) |
| C07C 235/34 | (2006.01) |
| C07H 1/08 | (2006.01) |

(52) U.S. Cl.
CPC ......... *C07H 15/203* (2013.01); *A61K 31/165* (2013.01); *A61P 25/00* (2018.01); *A61P 25/14* (2018.01); *A61P 25/16* (2018.01); *A61P 25/28* (2018.01); *A61P 31/14* (2018.01); *C07C 235/34* (2013.01); *C07H 1/08* (2013.01)

(58) Field of Classification Search
None
See application file for complete search history.

(56) References Cited

U.S. PATENT DOCUMENTS 6,576,642 B2  6/2003  Ishiwata et al.
9,012,687 B2  4/2015  Cheung et al.

FOREIGN PATENT DOCUMENTS

| CN | 102267922 A | 12/2011 |
| CN | 101300004 B | 8/2013 |
| CN | 104276973 A | 1/2015 |
| CN | 104418761 A | 3/2015 |
| CN | 105646611 A | 6/2016 |
| WO | 2007/035957 A2 | 3/2007 |
| WO | 2007/035957 A3 | 9/2007 |

OTHER PUBLICATIONS

Ho et al. "Anti-aging herbal medicine—How and why can they be used in aging-associated neurodegenerative diseases?" Ageing Research Reviews, 2010, vol. 9, pp. 354-362.*
Ren et al. "Dietary Supplementation with Lacto-Wolfberry Enhances the Immune Response and Reduces Pathogenesis to Influenza Infection in Mice" The Journal of Nutrition, 2012, vol. 142, No. 8, pp. 1596-1602.*
European Patent Office, Extended European Search Report for European Patent Application No. 1741001.6 dated Jul. 26, 2019, 10 pages.
Zheng, Jie, et al., "Anthocyanins composition and antioxidant activity of wild *Lycium ruthenicum* Murr. from Qinghai-Tibet Plateau," Food Chemistry, 2011, No. 126, pp. 859-865.
Zhou, Zheng-Qun, et al., "Lycibarbarspermidines A—O, New Dicaffeoylspermidine Derivatives from Wolfberry, with Activities against Alzheimer's Disease and Oxidation," Journal of Agircultural and Food Chemistry, 2016, No. 64, pp. 2223-2237.
Tully, Tim, and Quinn, William G., "Classical conditioning and retention in normal and mutant *Drosophila melanogaster*," Journal of Comparative Physiology A, 1985, vol. 157, pp. 263-277.
Tully, T., et al., "Genetic Dissection of Consolidated Memory in *Drosophila*," Cell, 1994, vol. 79, pp. 35-47.
Yin, J. C. P., et al., "Induction of a Dominant Negative CREB Transgene Specifically Blocks Long-Term Memory in *Drosophila*," Cell, 1994, vol. 79, pp. 49-58.
Patent Cooperation Treaty, International Search Report for International Application No. PCT/CN2017/071119 dated Apr. 12, 2017, and English Translation, 8 pages.
Patent Cooperation Treaty, Written Opinion for International Application No. PCT/CN2017/071119 dated Apr. 12, 2017, 4 pages.
Jin, Hongli, et al., "Preparative separation of a challenging anthocyanin from *Lycium ruthenicum* Murr. by two-dimensional reversed-phase liquid chromatography/hydrophilic interaction chromatography," The Royal Society of Chemistry, 2015, vol. 5, pp. 62134-62141.
Kosar, M., et al., "Determination of the Free Radical Scavenging Activity of Lycium Extracts," Chemistry of Natural Compounds, vol. 39, No. 6, 2003, pp. 531-535.

* cited by examiner

*Primary Examiner* — Joseph R Kosack
(74) *Attorney, Agent, or Firm* — Fitch, Even, Tabin & Flannery, LLP

(57) ABSTRACT

The present invention relates to dicaffeoyl spermidine derivative glycosides, a preparation method and a use thereof. The biological activity experiments show that the dicaffeoyl spermidine derivative glycosides of the present invention have anti-oxidative activity and antiviral activity, and their activity are even better than that of a positive control drug, thus can be used as an antioxidant for the prevention and/or treatment of neurodegenerative diseases such as Senile dementia, and as an antiviral agent for the prevention and/or treatment of viral infections.

5 Claims, No Drawings

DICAFFEOYL SPERMIDINE DERIVATIVE GLYCOSIDES AND USE THEREOF

CROSS-REFERENCE TO RELATED APPLICATIONS

This application is a U.S. national phase application filed under 35 U.S.C. § 371 of International Application Number PCT/CN2017/071119, filed Jan. 13, 2017, designating the United States, which claims priority from Chinese Patent Application Number 201610032769.0, filed Jan. 19, 2016.

TECHNICAL FIELD

The present invention belongs to the field of natural medicines, and more specifically relates to dicaffeoyl spermidine derivative glycosides and use thereof as an antioxidant and antiviral agent.

BACKGROUND OF THE INVENTION

Many processes of life activities involve the production and elimination of free radicals. Under normal physiological conditions, the production and elimination of free radicals in the organism is in equilibrium. Once the balance is imbalanced, excess free radicals will attack the target organs, resulting in lipid peroxidation of the cell membrane, breakage of the nucleic acid backbone, protein and polypeptide bonds, apoptosis, etc., causing body aging and degenerative changes of the organs, leading to the occurrence of various diseases such as cardiovascular and cerebrovascular diseases, cancer, diabetes, and senile dementia.

At present, numerous antioxidants have been used in food, pharmaceutical and cosmetic industries. For example, tea polyphenols extracted from tea are widely used in food additives and cosmetics, and their antioxidant capacity is 10 to 20 times higher than vitamin E; EGCG (epigallocatechin gallate), which has significant antioxidant capacity, is being developed as a drug for treating senile dementia; Flavonoids, such as luteolin, rutin and hesperidin, all have good antioxidant effects and can be used for prevention of cardiovascular disease and cancer. Therefore, the research and development of antioxidants has attracted increasing attention on food and drug industries. The ORAC analysis method has been widely recognized in the art as a standard analytical method to measure the antioxidant capacity of a substance, and has been approved by many research institutions such as the US Department of Agriculture and the National Institutes of Health. ORAC values have also become the international standard unit of antioxidant content of food.

Neurodegenerative diseases are one kind of chronic, progressive neurological diseases, generally characterized by delayed neuronal degenerative lesion and cell loss in specific regions. It is caused by the loss of neurons or their myelin sheath, and will worsen over time, resulting in dysfunction. The neurodegenerative diseases are generally divided into two categories according to their phenotype, one is affecting movement, such as cerebellar ataxia, Parkinson's disease, and the other is affecting memory and its related function, such as Dementia. At present, the therapeutic drug for neurodegenerative diseases is still fewer.

Senile dementia is one of the neurodegenerative diseases, and is heterogeneous disease with multiple etiologies. It is a central nervous system degenerative disease syndrome characterized by progressive cognitive dysfunction and memory impairment, behaving as a decrease in intelligence (including memory, learning ability, direction recognition ability, language ability, comprehension and judgment ability). This disease is affected by many factors (including biological and psychosocial factors). There are as many as 30 possible pathogenetic factors and hypotheses, such as family history, head trauma, thyroid disease, and viral infection. Senile dementia is commonly seen as Alzheimer's disease (AD), Vascular dementia (VA), Dementia with Lewy bodies (DLB), and Frontotemporal dementia (FTD). In all patients with dementia, Alzheimer's disease accounted for 50 to 70%, which is the most common type of Senile dementia.

The treatment of Senile dementia is mainly divided into: (1) the symptomatic treatment by controlling the concomitant psychopathological states with the medication mainly including anxiolytic drugs such as alprazolam, oxazepam, triazolam; antidepressants, such as Prozac, paroxetine, sertraline; antipsychotics such as risperidone, olanzapine; (2) the improvement of intelligence or cognitive function with the medication mainly including acetylcholinesterase inhibitors, N-methyl-D-aspartate receptor antagonists (NMDA), estrogens, and drugs for promoting brain metabolism. These drugs can improve the patient's dementia symptoms to a certain extent, but they cannot fundamentally prevent the deterioration of the disease and reverse the disease. Therefore, the search for anti-Senile dementia drugs has attracted worldwide attention, and many related biological activity screening and evaluation systems have been established. Among numerous existing whole animal models, fruit fly is one of the most well-known model organisms. The fruit fly has advantages that cannot be matched by other animal models, for example, extremely small individual space occupancy (in general, thousands fruit flies can be cultured in a single reagent bottle), low feeding costs, easy culture, rapid reproduction and strong reproductive capacity (high screening throughput), low sample consumption (5-50 mg), short life cycle (about 50 days, short activity test cycle), evident age-related neuronal deterioration. Thus it is desired model for the study and drug screening for neurodegenerative diseases such as Senile dementia.

Dicaffeoyl spermidine derivatives are a rare class of plant components that are currently under-researched. There have been no previous reports on dicaffeoyl spermidine derivative glycosides. The present invention is the discovery and isolation of a class of dicaffeoyl spermidine derivative glycosides from fructus lycii, and has been demonstrated by the experiment that it has the antioxidative and antiviral activities, and has the effects on degenerative diseases such as senile dementia.

SUMMARY OF THE INVENTION

An object of the present invention is to provide a class of dicaffeoyl spermidine derivative glycosides having the following structure formula, or pharmaceutically acceptable salts thereof,

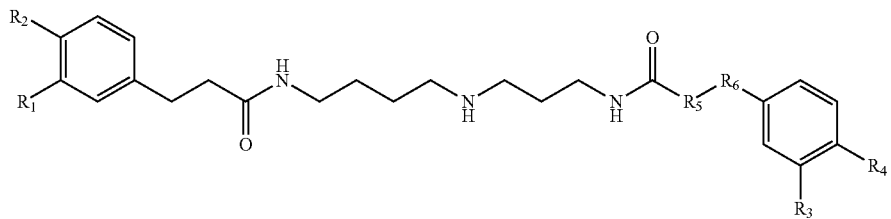

Formula (I)

wherein, $R_1$, $R_2$, $R_3$ and $R_4$ are hydroxy, methoxy, or optionally substituted glycosyl, and at least one of $R_1$, $R_2$, $R_3$ and $R_4$ is an optionally substituted glycosyl, $R_5$ and $R_6$ are both —CH= or —CH$_2$—, wherein the optionally substituted is optionally substituted with one or more of the following glycosyl groups: various monosaccharide groups such as glucosyl, glucuronyl, mannosyl, galactosyl, allosyl, fructosyl, sorbosyl, furanosyl, rhamnosyl, quinovosyl, arabinosyl, lyxosyl, xylosyl, ribosyl, and various disaccharide groups and polysaccharide groups formed by the above monosaccharides.

In a further embodiment of the present invention, the compound of formula (I) is preferably a compound having the following structural formula:

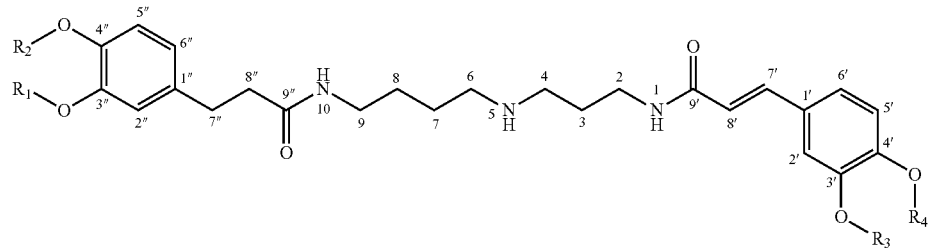

Formula (II): $R_1$ = H, $R_2$ = β-D-Glc, $R_3$ = H, $R_4$ = H
Formula (III): $R_1$ = H, $R_2$ = H, $R_3$ = β-D-Glc, $R_4$ = H
Formula (IV): $R_1$ = β-D-Glc, $R_2$ = H, $R_3$ = H, $R_4$ = H
Formula (V): $R_1$ = H, $R_2$ = H, $R_3$ = H; $R_4$ = β-D-Glc
Formula (VI): $R_1$ = H, $R_2$ = β-D-Glc, $R_3$ = β-D-Glc, $R_4$ = H
Formula (VII): $R_1$ = β-D-Glc, $R_2$ = H, $R_3$ = β-D-Glc, $R_4$ = H

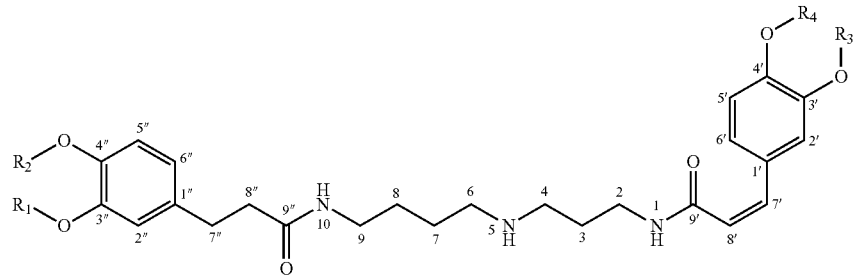

Formula (VIII): $R_1$ = H, $R_2$ = β-D-Glc, $R_3$ = β-D-Glc, $R_4$ = H

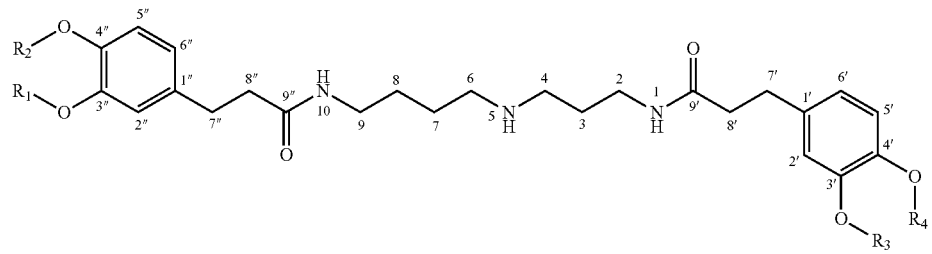

Formula (IX): $R_1$ = H, $R_2$ = H, $R_3$ = H, $R_4$ = β-D-Glc
Formula (X): $R_1$ = H, $R_2$ = β-D-Glc, $R_3$ = H, $R_4$ = H
Formula (XI): $R_1$ = H, $R_2$ = H, $R_3$ = β-D-Glc, $R_4$ = H
Formula (XII): $R_1$ = β-D-Glc, $R_2$ = H, $R_3$ = β-D-Glc, $R_4$ = H
Formula (XIII): $R_1$ = H, $R_2$ = β-D-Glc, $R_3$ = H, $R_4$ = β-D-Glc
Formula (XIV): $R_1$ = β-D-Glc, $R_2$ = H, $R_3$ = H, $R_4$ = β-D-Glc In the present invention, the pharmaceutically acceptable salts of the dicaffeoyl spermidine derivative glycosides of the formula (I) are salts formed by the dicaffeoyl spermidine derivative glycosides of the formula (I) with inorganic acids such as hydrochloric acid, hydrobromic acid, sulfuric acid, nitric acid, or with organic acids such as trifluoroacetic acid, acetic acid, propionic acid, malonic acid, butyric acid, lactic acid, methanesulfonic acid, ethanesulfonic acid, benzenesulfonic acid, p-toluenesulfonic acid, maleic acid, benzoic acid, succinic acid, picric acid, tartaric acid, citric acid, fumaric acid.

Another object of the present invention is to provide a use of dicaffeoyl spermidine derivative glycosides and the pharmaceutically acceptable salts thereof as antioxidants in manufacturing a medicament for preventing or treating neurodegenerative diseases, including but not limited to one or more of senile dementia, Parkinson's disease, multiple sclerosis and Huntington's disease, preferably senile dementia, more preferably, the senile dementia is Alzheimer's disease, vascular dementia, dementia with Lewy body or frontotemporal dementia.

A further object of the present invention is to provide a use of dicaffeoyl spermidine derivative glycosides and the pharmaceutically acceptable salts thereof in the preparation of antiviral agents with the virus being preferably a respiratory syncytial virus.

The dicaffeoyl spermidine derivative glycosides were isolated from the fructus lycii which is the fruit of *Lycium barbarum*. The fructus lycii is collected from Zhongning County, Ningxia Hui Autonomous Region, China. The samples were kept at the Institute of Traditional Chinese Medicine and Natural Medicines, College of Pharmacy, Jinan University (No. LYBA-2013-NX-ZN, Location: College of Pharmacy, Jinan University, 601 Huangpu Road West, Guangzhou 510632, China).

The method for preparing the dicaffeoyl spermidine derivative glycosides and pharmaceutically acceptable salts thereof specifically includes the following steps:

(1) The fructus lycii was extracted 3 times for 2 hours each time by heating under reflux with ethanol-water having the volume ratio of 60:40. After filtration, the filtrate was concentrated under reduced pressure to obtain a concentrated solution;

(2) The concentrated solution was chromatographed through a macroporous resin column and eluted successively with ethanol-water having the volume ratios of 0:100, 30:70, 50:50, 70:30, and 95:5 to obtain 5 fractions of F1, F2, F3, F4, and F5;

(3) The fraction F2, obtained by the elution with ethanol-water having the volume ratio of 30:70, was subjected to a silica gel column chromatography under normal pressure, and eluted successively with chloroform-methanol-water having the volume ratios of 95:5:0, 90:10:1, 85:15:1.5, 80:20:2, 70:30:3, 60:40:4, 50:50:5, 40:60:6 and 0:100:0 to obtain a total of 10 sub-fractions of F2.1, F2.2, F2.3, F2.4, F2.5, F2.6, F2.7, F2.8, F2.9 and F2.10;

(4) The sub-fraction F2.8, obtained by the elution with chloroform-methanol-water having the volume ratio of 50:50:5, was subjected to a low-medium pressure liquid phase ODS column chromatography, and eluted successively with methanol-water-trifluoroacetic acid having the volume ratios of 10:90:0.1, 15:85:0.1, 20:80:0.1, 25:75:0.1, 30:70:0.1, 40:60:0.1 and 100:0:0 to obtain a total of 8 sub-fractions of F2.8.1, F2.8.2, F2.8.3, F2.8.4, F2.8.5, F2.8.6, F2.8.7, and F2.8.8;

(5) The sub-fraction F2.8.1, obtained by the elution with methanol-water-trifluoroacetic acid having the volume ratio of 10:90:0.1, was subjected to a reversed phase preparative HPLC (Cosmosil Packed C18 column), and eluted with methanol-water-trifluoroacetic acid having the volume ratio of 20:80:0.1 at a flow rate of 8 mL/min, to obtain a total of 5 sub-fractions of F2.8.1.1, F2.8.1.2, F2.8.1.3, F2.8.1.4, and F2.8.1.5;

(6) The sub-fraction F2.8.1.3 was subjected to a reversed phase preparative HPLC (Cosmosil Packed C18 column), and eluted with acetonitrile-water-trifluoroacetic acid having the volume ratio of 10:90:0.1 at a flow rate of 8 mL/min, to obtain the trifluoroacetate salt of the compound of formula (XI);

(7) The sub-fraction F2.8.1.4 was subjected to a reversed phase preparative HPLC (Phenomex Gemini C18 column), and eluted with methanol-water-trifluoroacetic acid having the volume ratio of 20:80:0.1 at a flow rate of 8 mL/min, to obtain the trifluoroacetate salt of the compound of formula (II);

(8) The sub-fraction F2.8.1.5 was subjected to a reversed phase preparative HPLC (Cosmosil Packed C18 column), and eluted with acetonitrile-water-trifluoroacetic acid having the volume ratio of 10:90:0.1 at a flow rate of 8 mL/min, to obtain the trifluoroacetate salts of the compound of formula (III) and the compound of formula (IV);

(9) The sub-fraction F2.9, obtained by the elution with chloroform-methanol-water having the volume ratio of 40:60:6, was subjected to a low-medium pressure liquid phase ODS column chromatography, and eluted successively with methanol-water-trifluoroacetic acid having the volume ratio of 5:95:0.1, 10:90:0.1, 15:85:0.1, 20:80:0.1, 25:75:0.1, 30:70:0.1, 40:60:0.1 and 100:0:0 to obtain a total of 9 sub-fractions of F2.9.1, F2.9.2, F2.9.3, F2.9.4, F2.9.5, F2.9.6, F2.9.7, F2.9.8, and F2.9.9;

(10) The sub-fraction F2.9.2, obtained by the elution with methanol-water-trifluoroacetic acid having the volume ratio of 10:90:0.1, was subjected to a reversed phase preparative HPLC (Cosmosil Packed C18 column), and eluted with methanol-water-trifluoroacetic acid having the volume ratio of 18:82:0.1 at a flow rate of 8 mL/min, to obtain a total of 6 sub-fractions of F2.9.2.1, F2.9.2.2, F2.9.2.3, F2.9.2.4, F2.9.2.5, and F2.9.2.6;

(11) The sub-fraction F2.9.2.4 was subjected to a reversed phase preparative HPLC (Cosmosil Packed C18 column), and eluted with acetonitrile-water-trifluoroacetic acid at a flow rate of 8 mL/min having the volume ratio of 10:90:0.1, to obtain the trifluoroacetate salt of the compound of formula (XIII);

(12) The sub-fraction F2.9.2.5 was subjected to a reversed phase preparative HPLC (Cosmosil Packed C18 column), and eluted with acetonitrile-water-trifluoroacetic acid having the volume ratio of 12:88:0.1 at a flow rate of 8 mL/min, to obtain the trifluoroacetate salt of the compound of formula (VIII);

(13) The sub-fraction F2.9.3, obtained by the elution with methanol-water-trifluoroacetic acid having the volume ratio of 10:90:0.1, was subjected to a reversed phase preparative HPLC (Cosmosil Packed C18 column), and eluted with methanol-water-trifluoroacetic acid having the volume ratio of 18:82:0.1 at a flow rate of 8 mL/min, to obtain a total of 6 sub-fractions of F2.9.3.1, F2.9.3.2, F2.9.3.3, F2.9.3.4, F2.9.3.5, and F2.9.3.6;

(14) The sub-fraction F2.9.3.3 was subjected to a reversed phase preparative HPLC (Phenomex Gemini C18 column), and eluted with methanol-water-ammonia having the volume ratio of 15:85:0.1 at a flow rate of 8 mL/min, to obtain the compound of formula (XIV).

(15) The sub-fraction F2.9.3.5 was subjected to a reversed phase preparative HPLC (Cosmosil Packed C18 column), and eluted with acetonitrile-water-trifluoroacetic acid having the volume ratio of 10:90:0.1 at a flow rate of 8 mL/min, to obtain the trifluoroacetate salt of the compound of formula (XII);

(16) The sub-fraction F2.9.3.6 was subjected to a reversed phase preparative HPLC (Cosmosil Packed C18 column), and eluted with acetonitrile-water-trifluoroacetic acid having the volume ratio of 12:88:0.1 at a flow rate of 8 mL/min, to obtain the trifluoroacetate salt of the mixture of the compound of formula (IX) and the compound of formula (X);

(17) The sub-fraction F2.9.5, obtained by the elution with methanol-water-trifluoroacetic acid having the volume ratio of 15:85:0.1, was subjected to a reversed phase preparative HPLC (Cosmosil Packed C18 column), and eluted with methanol-water-trifluoroacetic acid having the volume ratio of 20:80:0.1 at a flow rate of 8 mL/min, to obtain a total of 4 sub-fractions of F2.9.5.1, F2.9.5.2, F2.9.5.3 and F2.9.5.4;

(18) The sub-fraction F2.9.5.1 was subjected to a reversed phase preparative HPLC (Cosmosil Packed C18 column), and eluted with acetonitrile-water-trifluoroacetic acid having the volume ratio of 10:90:0.1 at a flow rate of 8 mL/min, to obtain the trifluoroacetate salts of the compound of formula (V) and the compound of formula (VI);

(19) The sub-fraction F2.9.5.2 was subjected to a reversed phase preparative HPLC (Phenomex Gemini C18 column), and eluted with methanol-water-ammonia having the volume ratio of 15:85:0.1 at a flow rate of 8 mL/min, to obtain the compound of formula (VII).

Still another object of the present invention is to provide an anti-oxidative pharmaceutical composition for preventing or treating neurodegenerative diseases and to provide an antiviral pharmaceutical composition for preventing or treating viral infectious diseases, said pharmaceutical composition comprises compounds of formula (I) or pharmaceutically acceptable salts thereof as active ingredients and pharmaceutically acceptable excipients.

Preferred compounds of formula (I) are compounds of formula (II) to formula (XIV) or pharmaceutically acceptable salts thereof, the pharmaceutically acceptable excipients include, but are not limited to, diluents, lubricants, binders, disintegrants, stabilizers, solvents, and the like.

The diluents of the present invention include but are not limited to starch, microcrystalline cellulose, sucrose, dextrin, lactose, powdered sugar, glucose, and the like.

The lubricants include but are not limited to magnesium stearate, stearic acid, sodium chloride, sodium oleate, sodium lauryl sulfate, poloxamer, and the like.

The binders include but are not limited to water, ethanol, starch slurry, syrup, hydroxypropyl methylcellulose, sodium carboxymethylcellulose, sodium alginate, polyvinylpyrrolidone, and the like.

The disintegrants include but are not limited to starch effervescent mixtures, i.e., sodium bicarbonate and citric acid, tartaric acid, low substituted hydroxypropyl cellulose, and the like.

The stabilizers include but are not limited to polysaccharides such as acacia, agar, alginic acid, cellulose ether, and carboxymethyl chitin.

The solvents include but are not limited to water, balanced salt solution, and the like.

The pharmaceutical composition of the present invention may be administered orally or by injection. The corresponding dosage form of the pharmaceutical composition includes, but is not limited to, solid oral formulations, liquid oral formulations, injections and the like.

The preferred solid oral formulations include tablets, granules, capsules, dripping pills, powders, and the like. The liquid oral formulations include oral liquids, emulsions, and the like.

The injections include small water injections, large infusions, lyophilized powders for injection, and the like.

More preferred tablets include dispersible tablets, enteric tablets and the like.

The formulations of the present invention can be prepared according to conventional techniques in the pharmaceutical arts.

The amount of the active ingredient (i.e., the compound of the present invention) contained in the pharmaceutical formulation of the present invention can be used specifically according to the condition of the patient and the doctor's diagnosis. The dose or concentration of the active compound is adjusted within a relatively wide range. The content of the active compound ranges from 1% to 90% by weight of the pharmaceutical composition.

Beneficial Effects

Compared with the prior art, the present invention has the following advantages and beneficial effects: the dicaffeoyl spermidine derivative glycosides shown in the present invention are novel dicaffeoyl spermidine derivative glycosides. The present invention demonstrated by the biological activity test experiments that the dicaffeoyl spermidine derivative glycosides of the present invention have antioxidant activity, and proved through drosophila animal model that it has anti-senile dementia effect, and also has anti-respiratory syncytial virus (RSV) activity. The activity of most compounds is even better than that of a positive control drug or equivalent to a positive control drug. These novel dicaffeoyl spermine derivative glycosides are suitable for use as antioxidants, and can significantly improve the cognitive function under senile dementia disease state, inhibit the viruses proliferation and prevent or treat the related diseases.

DETAILED DESCRIPTION OF THE INVENTION

The following examples are intended to illustrate the present invention without limiting it further. The present invention can be implemented in any of the ways described in the Summary of the Invention.

In the following examples, the mass spectrometer was a LCQ Advantage MAX mass spectrometer manufactured by Finnigan, Germany. The superconducting NMR spectrometers were Bruker AV-300, Bruker AV-400 and Bruker AV-600. Column chromatography HP-20 macroporous resin is a product of Japan's Mitsubishi Corporation. Thin-layer chromatography silica gel GF254 and column chromatography silica gel (200-300 mesh) are both products of Qingdao Ocean Chemical Factory. The reversed phase ODS filler (50 μm) is a product of YMC Japan. The low-medium pressure liquid chromatography is a product of Shanghai Lisui Electronic Technology Co., Ltd. The preparative column used for the liquid phase separation was a Phenomex Gemini C18 column (21.2×250 mm, 5 μm) or a Cosmosil Packed C18 column (20.0×250 mm, 5 μm). The acetonitrile or methanol for liquid chromatography is chromatographic grade, the water is double distilled water, and the other reagents are analytical grade.

Example 1 Preparation of Compounds of Formula (II)—Formula (XIV)

The 19.5 kg fructus lycii was extracted 3 times for 2 hours each time by heating under reflux with 100 L ethanol-water (60:40, v/v). After filtration, the filtrate was concentrated under reduced pressure to obtain a concentrated solution. The concentrated solution was chromatographed through a macroporous resin column, and eluted successively with ethanol-water having the volume ratios of 0:100, 30:70, 50:50, 70:30, and 95:5, and 5 fractions of F1, F2, F3, F4, F5 were obtained. Then the fraction F2, obtained by the elution with ethanol-water having the volume ratio of 30:70, was subjected to a silica gel column chromatography under normal pressure by using 70.0 g of F2, and eluted successively with chloroform-methanol-water having the volume ratios of 95:5:0, 90:10:1, 85:15:1.5, 80:20:2, 70:30:3, 60:40:4, 50:50:5, 40:60:6 and 0:100:0, a total of 10 sub-fractions of F2.1, F2.2, F2.3, F2.4, F2.5, F2.6, F2.7, F2.8, F2.9 and F2.10 were obtained. Subsequently, the sub-fraction F2.8 (10.1 g), obtained by the elution with chloroform-methanol-water having the volume ratio of 50:50:5, was subjected to a low-medium pressure liquid phase ODS column chromatography, and eluted successively with methanol-water-trifluoroacetic acid having the volume ratios of 10:90:0.1, 15:85:0.1, 20:80:0.1, 25:75:0.1, 30:70:0.1, 40:60:0.1 and 100:0:0, a total of 8 sub-fractions of F2.8.1, F2.8.2, F2.8.3, F2.8.4, F2.8.5, F2.8.6, F2.8.7, and F2.8.8 were obtained. The sub-fraction F2.8.1 (0.5 g), obtained by the elution with methanol-water-trifluoroacetic acid having the volume ratio of 10:90:0.1, was subjected to a reversed phase preparative HPLC (Cosmosil Packed C18 column), eluted with methanol-water-trifluoroacetic acid at a flow rate of 8 mL/min (20:80:0.1, v/v/v), and a total of 5 sub-fractions of F2.8.1.1, F2.8.1.2, F2.8.1.3, F2.8.1.4 and F2.8.1.5 were obtained. The sub-fraction F2.8.1.3 (48.3 mg) was subjected to a reversed phase preparative HPLC (Cosmosil Packed C18 column), and eluted with acetonitrile-water-trifluoroacetic acid (10:90:0.1, v/v/v) at a flow rate of 8 mL/min, the trifluoroacetate salt of the compound of formula (XI) ($t_R$: 75.8 min, 10.0 mg, purity 95%) was obtained. The sub-fraction F2.8.1.4 (153.5 mg) was subjected to a reversed phase preparative HPLC (Phenomex Gemini C18 column), and eluted with methanol-water-trifluoroacetic acid (20:80:0.1, v/v/v) at a flow rate of 8 mL/min, the trifluoroacetate salt of the compound of formula (II) ($t_R$: 104.5 min, 129.9 mg, purity 95%) was obtained. The sub-fraction F2.8.1.5 (87.6 mg) was subjected to a reversed phase preparative HPLC (Cosmosil Packed C18 column), and eluted with acetonitrile-water-trifluoroacetic acid (10:90:0.1, v/v/v) at a flow rate of 8 mL/min, the trifluoroacetate salts of the compound of formula (III) ($t_R$: 117.7 min, 44.6 mg, purity 95%) and the compound of formula (IV) ($t_R$: 131.5 min, 6.0 mg, purity 95%) were obtained.

Similarly, the sub-fraction F2.9 (3.8 g), obtained by the elution with chloroform-methanol-water having the volume ratio of 40:60:6, was subjected to a low-medium pressure liquid phase ODS column chromatography, and eluted successively with methanol-water-trifluoroacetic acid having the volume ratios of 5:95:0.1, 10:90:0.1, 15:85:0.1, 20:80:0.1, 25:75:0.1, 30:70:0.1, 40:60:0.1 and 100:0:0, a total of 9 sub-fractions of F2.9.1, F2.9.2, F2.9.3, F2.9.4, F2.9.5, F2.9.6, F2.9.7, F2.9.8 and F2.9.9 were obtained. The sub-fraction F2.9.2 (170.6 g), obtained by the elution with methanol-water-trifluoroacetic acid having the volume ratio of 10:90:0.1, was subjected to a reversed phase preparative HPLC (Cosmosil Packed C18 column), eluted with methanol-water-trifluoroacetic acid (18:82:0.1, v/v/v) at a flow rate of 8 mL/min, and a total of 6 sub-fractions of F2.9.2.1, F2.9.2.2, F2.9.2.3, F2.9.2.4 F2.9.2.5 and F2.9.2.6 were obtained. The sub-fraction F2.9.2.4 (41.0 mg) was subjected to a reversed phase preparative HPLC (Cosmosil Packed C18 column), and eluted with acetonitrile-water-trifluoroacetic acid (10:90:0.1, v/v/v) at a flow rate of 8 mL/min, the trifluoroacetate salt of the compound of formula (XIII) ($t_R$: 32.0 min, 29.7 mg, purity 95%) was obtained. The sub-fraction F2.9.2.5 (97.3 mg) was subjected to a reversed phase preparative HPLC (Cosmosil Packed C18 column), and eluted with acetonitrile-water-trifluoroacetic acid (12:88:0.1, v/v/v) at a flow rate of 8 mL/min, the trifluoroacetate salt of the compound of formula (VIII) ($t_R$: 19.3 min, 30.4 mg, purity 95%) was obtained. The sub-fraction F2.9.3 (239.0 mg), obtained by the elution with methanol-water-trifluoroacetic acid having the volume ratio of 10:90:0.1, was subjected to a reversed phase preparative HPLC (Cosmosil Packed C18 column), and eluted with methanol-water-trifluoroacetic acid (18:82:0.1, v/v/v) at a flow rate of 8 mL/min, a total of 6 sub-fractions of F2.9.3.1, F2.9.3.2, F2.9.3.3, F2.9.3.4 F2.9.3.5 and F2.9.3.6 were obtained. The sub-fraction F2.9.3.3 (40.1 mg) was subjected to a reversed phase preparative HPLC (Phenomex Gemini C18 column), and eluted with methanol-water-ammonia (15:85:0.1, v/v/v) at a flow rate of 8 mL/min, the compound of formula (XIV) ($t_R$: 59.0 min, 23.9 mg, purity 95%) was obtained.

The sub-fraction F2.9.3.5 (32.0 mg) was subjected to a reversed phase preparative HPLC (Cosmosil Packed C18 column), and eluted with acetonitrile-water-trifluoroacetic acid (10:90:0.1, v/v/v) at a flow rate of 8 mL/min, the trifluoroacetate salt of the compound of formula (XII) ($t_R$: 44.3 min, 17.6 mg, purity 95%) was obtained. The sub-fraction F2.9.3.6 (103.8 mg) was subjected to a reversed phase preparative HPLC (Cosmosil Packed C18 column), and eluted with acetonitrile-water-trifluoroacetic acid (12:88:0.1, v/v/v) at a flow rate of 8 mL/min, the trifluoroacetate salt of the mixture of the compound of formula (IX) and the compound of formula (X) ($t_R$: 25.8 min, 69.2 mg, purity 95%) was obtained. The sub-fraction F2.9.5 (344.6 mg), obtained by the elution with methanol-water-trifluoroacetic acid having the volume ratio of 15:85:0.1, was subjected to a reversed phase preparative HPLC (Cosmosil Packed C18 column), and eluted with methanol-water-trifluoroacetic acid (20:80:0.1, v/v/v) at a flow rate of 8 mL/min, a total of 4 sub-fractions of F2.9.5.1, F2.9.5.2, F2.9.5.3 and F2.9.5.4 were obtained. The sub-fraction F2.9.5.1 (31.8 mg) was subjected to a reversed phase preparative HPLC (Cosmosil Packed C18 column), and eluted with acetonitrile-water-trifluoroacetic acid (10:90:0.1, v/v/v) at a flow rate of 8 mL/min, the trifluoroacetate salts of the compound of formula (V) ($t_R$: 53.0 min, 7.2 mg, purity 95%) and compound of formula (VI) ($t_R$: 49.5 min, 8.0 mg, purity 95%) were obtained. The sub-fraction F2.9.5.2 (159.5 mg) was subjected to a reversed phase preparative HPLC (Phenomex Gemini C18 column), and eluted with methanol-water-ammonia (15:85:0.1, v/v/v) at a flow rate of 8 mL/min, the compound of formula (VII) ($t_R$: 44.3 min, 122.0 mg, purity 95%) was obtained.

The physicochemical constants are as follows:

The trifluoroacetate salt of the compound of formula (II): green oily liquid; $[\alpha]_D^{27}$ −25.1 (c 0.50, MeOH); UV (MeOH) $\lambda_{max}$ (log ε) 204 (4.54), 219 (4.28), 287 (4.06), 290 (4.06), 325 (4.13) nm; IR (KBr) $v_{max}$ 3219, 2948, 1678, 1509, 1437, 1284, 1205, 1132, 1074, 801, 723 cm$^{-1}$; ESIMS (positive) m/z 634.4; ESIMS (negative) m/z 632.5; HRESIMS (positive) m/z 634.2978 (calcd. for $C_{31}H_{44}N_3O_{11}$, 634.2976), and the molecular formula of this compound was identified as $C_{31}H_{43}N_3O_{11}$; $^{13}C$ and $^1H$ NMR are shown in Table 1.

The trifluoroacetate salt of the compound of formula (III): green oily liquid; $[\alpha]_D^{27}$ −25.6 (c 0.50, MeOH); UV (MeOH) $\lambda_{max}$ (log ε) 204 (4.52), 232, (4.25), 292 (4.23), 315 (4.25) nm; IR (KBr) $v_{max}$ 3283, 2870, 1687, 1508, 1281, 1200, 1137, 1068, 860, 724 cm$^{-1}$; ESIMS (positive) m/z 634.5; ESIMS (negative) m/z 632.6; HRESIMS (positive) m/z 634.2969 (calcd. for $C_{31}H_{44}N_3O_{11}$, 634.2976), and the molecular formula of this compound was identified as $C_{37}H_{43}N_3O_{11}$; $^{13}C$ and $^1H$ NMR are shown in Table 1.

The trifluoroacetate salt of the compound of formula (IV): green oily liquid; $[\alpha]_D^{27}$ −21.4 (c 0.50, MeOH); UV (MeOH) $\lambda_{max}$ (log ε) 203 (4.43), 288 (3.95), 325 (4.02) nm; IR (KBr) $v_{max}$ 3314, 2935, 2868, 1680, 1517, 1439, 1283, 1204, 1137, 1075, 802, 722 cm$^{-1}$; ESIMS (positive) m/z 634.6; ESIMS (negative) m/z 632.5; HRESIMS (positive) m/z 634.2966 (calcd. for $C_{31}H_{44}N_3O_{11}$, 634.2976), and the molecular formula of this compound was identified as $C_{31}H_{43}N_3O_{11}$; $^{13}C$ and $^1H$ NMR are shown in Table 1.

The trifluoroacetate salt of the compound of formula (V): green oily liquid; $[\alpha]_D^{27}$ −21.0 (c 0.50, MeOH); UV (MeOH) $\lambda_{max}$ (log ε) 204 (4.50), 218 (4.24), 233 (4.11), 287 (4.21), 316 (4.06) nm; IR (KBr) $v_{max}$ 3344, 2933, 2871, 1675, 1515, 1439, 1269, 1199, 1137, 1070, 802, 722 cm$^{-1}$; ESIMS (positive) m/z 634.5; ESIMS (negative) m/z 632.4; HRESIMS (positive) m/z 634.2979 (calcd. for $C_{31}H_{44}N_3O_{11}$, 634.2976), and the molecular formula of this compound was identified as $C_{31}H_{43}N_3O_{11}$; $^{13}C$ and $^1H$ NMR are shown in Table 1.

The trifluoroacetate salt of the compound of formula (VI): green oily liquid; $[\alpha]_D^{27}$ −33.6 (c 0.50, MeOH); UV (MeOH) $\lambda_{max}$ (log ε) 204 (4.52), 294 (4.10), 315 (4.13) nm; IR (KBr) $v_{max}$ 3314, 2931, 2876, 1677, 1509, 1437, 1280, 1205, 1136, 1077, 801, 722 cm$^{-1}$; ESIMS (positive) m/z 796.7; ESIMS (negative) m/z 794.6; HRESIMS (positive) m/z 796.3482 (calcd. for $C_{37}H_{54}N_3O_{16}$, 796.3504), and the molecular formula of this compound was identified as $C_{37}H_{53}N_3O_{16}$; $^{13}C$ and $^1H$ NMR are shown in Table 1.

The compound of formula (VII): green oily liquid; $[\alpha]_D^{27}$ −18.7 (c 0.50, MeOH); UV (MeOH) $\lambda_{max}$ (log ε) 204 (4.17), 288 (3.62), 313 (3.62) nm; IR (KBr) $v_{max}$ 3295, 2928, 2876, 1649, 1496, 1438, 1282, 1231, 1063, 825, 722 cm$^{-1}$; ESIMS (positive) m/z 796.6; ESIMS (negative) m/z 794.7; HRESIMS (positive) m/z 796.3517 (calcd. for $C_{37}H_{54}N_3O_{16}$, 796.3504), and the molecular formula of this compound was identified as $C_{37}H_{53}N_3O_{16}$; $^{13}C$ and $^1H$ NMR are shown in Table 2.

The trifluoroacetate salt of the compound of formula (VIII): green oily liquid; $[\alpha]_D^{27}$ −25.0 (c 0.50, MeOH); UV (MeOH) $\lambda_{max}$ (log ε) 204 (4.42), 281 (3.83), 314 (3.71) nm; IR (KBr) $v_{max}$ 3329, 2930, 2874, 1681, 1509, 1435, 1283, 1206, 1132, 1071, 802, 722 cm$^{-1}$; ESIMS (positive) m/z 796.4; HRESIMS (positive) m/z 796.3517 (calcd. for $C_{37}H_{54}N_3O_{16}$, 796.3504), and the molecular formula of this compound was identified as $C_{37}H_{53}N_3O_{16}$; $^{13}C$ and $^1H$ NMR are shown in Table 2.

The trifluoroacetate salts of the compounds of formula (IX) and formula (X): green oily liquid; $[\alpha]_D^{27}$ −19.0 (c 0.50, MeOH); UV (MeOH) $\lambda_{max}$ (log ε) 205 (4.59), 281 (3.66) nm; IR (KBr) $v_{max}$ 3311, 2934, 2867, 1681, 1509, 1438, 1283, 1206, 1134, 1075, 801, 723 cm$^{-1}$; ESIMS (positive) m/z 636.5; HRESIMS (positive) m/z 636.3129 (calcd. for $C_{31}H_{46}N_3O_{11}$, 636.3132), and the molecular formula of the compound was identified as $C_{31}H_{45}N_3O_{11}$; $^{13}C$ and $^1H$ NMR are shown in Table 2.

The trifluoroacetate salt of the compound of formula (XI): green oily liquid; $[\alpha]_D^{27}$ −22.6 (c 0.50, MeOH); UV (MeOH) $\lambda_{max}$ (log ε) 204 (4.49), 224 (3.97), 282 (3.60) nm; IR (KBr) $v_{max}$ 3302, 2931, 2871, 1681, 1511, 1436, 1206, 1140, 1076, 801, 723 cm$^{-1}$; ESIMS (positive) m/z 636.5; ESIMS (negative) m/z 634.7; HRESIMS (positive) m/z 636.3128 (calcd. for $C_{31}H_{46}N_3O_{11}$, 636.3132), and the molecular formula of this compound was identified as $C_{31}H_{45}N_3O_{11}$; $^{13}C$ and $^1H$ NMR are shown in Table 2.

The trifluoroacetate salt of the compound of formula (XII): green oily liquid; $[\alpha]_D^{27}$ −17.3 (c 0.50, MeOH); UV (MeOH) $\lambda_{max}$ (log ε) 204 (4.68), 280 (3.68) nm; IR (KBr) $v_{max}$ 3341, 2933, 2881, 1675, 1516, 1440, 1283, 1194, 1064, 801, 723 cm$^{-1}$; ESIMS (positive) m/z 798.5; HRESIMS (positive) m/z 798.3661 (calcd. for $C_{37}H_{56}N_3O_{16}$, 798.3661), and the molecular formula of this compound was identified as $C_{37}H_{55}N_3O_{16}$; $^{13}C$ and $^1H$ NMR are shown in Table 3.

The trifluoroacetate salt of the compound of formula (XIII): green oily liquid; $[\alpha]_D^{27}$ −28.5 (c 0.50, MeOH); UV (MeOH) $\lambda_{max}$ (log ε) 204 (4.51), 279 (3.52) nm; IR (KBr) $v_{max}$ 3342, 2930, 2874, 1682, 1508, 1436, 1281, 1207, 1133, 1071, 801, 722 cm$^{-1}$; ESIMS (positive) m/z 798.6; HRESIMS (positive) m/z 798.3664 (calcd. for $C_{37}H_{56}N_3O_{16}$, 798.3661), and the molecular formula of this compound was identified as $C_{37}H_{55}N_3O_{16}$; $^{13}C$ and $^1H$ NMR are shown in Table 3.

The compound of formula (XIV): green oily liquid; $[\alpha]_D^{27}$ −25.5 (c 0.50, MeOH); UV (MeOH) $\lambda_{max}$ (log ε) 205 (4.68), 279 (3.74) nm; IR (KBr) $v_{max}$ 3353, 2928, 2868, 1648, 1508, 1283, 1076, 815 cm$^{-1}$; ESIMS (positive) m/z 798.7; ESIMS (negative) m/z 796.7; HRESIMS (positive) m/z 798.3632 (calcd. for $C_{37}H_{56}N_3O_{16}$, 798.3661), and the molecular formula of this compound was identified as $C_{37}H_{55}N_3O_{16}$; $^{13}C$ and $^1H$ NMR are shown in Table 3.

TABLE 1

$^{13}C$ NMR and $^1H$ NMR data and attributions of compounds of formula (II)-formula (VI).

| | formula II | | formula III | | formula IV | | formula V | | formula VI | |
|---|---|---|---|---|---|---|---|---|---|---|
| No. | $\delta_C^a$ | $\delta_H^a$ | $\delta_C^a$ | $\delta_H^a$ | $\delta_C^a$ | $\delta_H^a$ | $\delta_C^a$ | $\delta_H^a$ | $\delta_C^a$ | $\delta_H^a$ |
| 1 | | 8.21, t (5.7) | | 8.14, t (5.9) | | 8.17, t (5.3) | | 8.22, br s | | 8.10, t (5.8) |
| 2 | 35.8 | 3.23, q (6.4) | 35.8 | 3.24, q (6.5) | 35.7 | 3.23, q (6.4) | 35.8 | 3.24, q (5.7) | 35.8 | 3.24, m |
| 3 | 26.2 | 1.78, quint (6.7) | 26.2 | 1.78, quint (6.8) | 26.2 | 1.77, quint (7.1) | 26.2 | 1.77, quint (6.8) | 26.2 | 1.77, quint (6.8) |
| 4 | 44.8 | 2.90, m | 44.7 | 2.89, m | 44.7 | 2.89 m | 44.7 | 2.90, m | 44.7 | 2.89, m |
| 5 | | 8.46, br s | | 8.47, br s | | 8.34, br s | | 8.34, br s | | 8.35, br s |
| 6 | 46.6 | 2.88, m | 46.5 | 2.88, m | 46.5 | 2.89, m | 46.5 | 2.89, m | 46.5 | 2.89, m |

TABLE 1-continued $^{13}$C NMR and $^1$H NMR data and attributions of compounds of formula (II)-formula (VI).

| No. | formula II $\delta_C{}^a$ | formula II $\delta_H{}^a$ | formula III $\delta_C{}^a$ | formula III $\delta_H{}^a$ | formula IV $\delta_C{}^a$ | formula IV $\delta_H{}^a$ | formula V $\delta_C{}^a$ | formula V $\delta_H{}^a$ | formula VI $\delta_C{}^a$ | formula VI $\delta_H{}^a$ |
|---|---|---|---|---|---|---|---|---|---|---|
| 7 | 23.1 | 1.53, quint (7.1) | 23.1 | 1.53, quint (7.1) | 23.1 | 1.51, quint (6.8) | 23.1 | 1.53, quint (6.7) | 23.1 | 1.53, quint (7.1) |
| 8 | 26.3 | 1.42, quint (6.8) | 26.2 | 1.41, quint (7.3) | 26.2 | 1.41, quint (7.4) | 26.2 | 1.42, quint (6.7) | 26.2 | 1.42, quint (7.0) |
| 9 | 37.8 | 3.04, q (6.5) | 37.7 | 3.04, q (6.1) | 37.7 | 3.04, q (6.1) | 37.7 | 3.04, q (6.5) | 37.7 | 3.04, q (6.1) |
| 10 | | 7.86, t (5.6) | | 7.83 t (5.6) | | 7.81, t (5.5) | | 7.82, t (5.5) | | 7.84, t (5.7) |
| 1' | 126.3 | | 126.4 | | 126.2 | | 129.4 | | 126.4 | |
| 2' | 113.9 | 6.95, d (1.9) | 115.8 | 7.35, d (1.7) | 113.8 | 6.94, m | 114.1 | 7.02, d (1.6) | 115.8 | 7.35, d (1.9) |
| 3' | 145.6 | | 145.5 | | 145.5 | | 146.9 | | 145.5 | |
| 4' | 147.5 | | 148.5 | | 147.4 | | 146.7 | | 148.5 | |
| 5' | 115.8 | 6.75, d (8.1) | 116.2 | 6.84, d (8.2) | 115.7 | 6.75, d (8.1) | 116.3 | 7.11, d (8.4) | 116.2 | 6.84, d (8.2) |
| 6' | 120.5 | 6.84, dd (8.2, 1.9) | 123 | 7.10, dd (8.2, 1.6) | 120.5 | 6.84, dd (8.2, 1.9) | 119.9 | 6.96, dd (8.5, 1.8) | 122.9 | 7.11, dd (8.4, 1.9) |
| 7' | 139.5 | 7.26, d (15.7) | 139.2 | 7.32, d (15.7) | 139.5 | 7.26, d (15.6) | 138.9 | 7.31, d (15.7) | 139.3 | 7.32, d (15.7) |
| 8' | 118 | 6.32, d (15.7) | 118.8 | 6.41, d (15.8) | 118 | 6.31, d (15.7) | 119.9 | 6.43, d (15.5) | 118.8 | 6.39, d (15.7) |
| 9' | 166 | | 165.9 | | 166 | | 165.7 | | 165.9 | |
| 1" | 136.3 | | 132.1 | | 132.2 | | 132.1 | | 136.2 | |
| 2" | 115.8 | 6.65, d (2.0) | 115.6 | 6.56, d (1.9) | 116.8 | 6.95, m | 115.6 | 6.55, d (1.9) | 115.8 | 6.64, d (2.1) |
| 3" | 146.7 | | 145 | | 145 | | 144.9 | | 146.6 | |
| 4" | 143.6 | | 143.3 | | 144.9 | | 143.3 | | 143.6 | |
| 5" | 117 | 6.99, d (8.2) | 115.4 | 6.61, d (8.0) | 115.6 | 6.70, d (8.1) | 115.4 | 6.60, d (7.9) | 116.9 | 6.99, d (8.3) |
| 6" | 118.9 | 6.54, dd (8.3, 1.9) | 118.7 | 6.41, m | 122.4 | 6.68, dd (8.2, 1.6) | 118.7 | 6.41, dd (7.9, 2.0) | 118.9 | 6.54, dd (8.2, 2.0) |
| 7" | 30.6 | 2.68, t (7.4) | 30.6 | 2.61, t (7.5) | 30.5 | 2.68, td (7.5, 2.9) | 30.6 | 2.62, t (7.4) | 30.6 | 2.68, t (7.4) |
| 8" | 37.2 | 2.30, t (7.5) | 37.6 | 2.26, t (7.4) | 37.1 | 2.31, t (7.8) | 37.6 | 2.26, t (7.5) | 37.2 | 2.30, t (7.4) |
| 9" | 171.4 | | 171.5 | | 171.4 | | 171.5 | | 171.3 | |
| 1''' | 102.8 | 4.59, d (7.3) | 102.1 | 4.74, d (7.3) | 102.4 | 4.62, d (7.3) | 101.7 | 4.75, d (7.3) | 102.1 | 4.74, d (7.4) |
| 2''' | 73.4 | 3.27, m | 73.3 | 3.31, m | 73.3 | 3.28, m | 73.2 | 3.30, m | 73.3 | 3.28, m |
| 3''' | 75.9 | 3.27, m | 76 | 3.29, m | 75.9 | 3.27, m | 75.8 | 3.28, m | 76.0*[1] | 3.28, m |
| 4''' | 69.9 | 3.16, m | 69.9 | 3.18, m | 69.8 | 3.16, m | 69.8 | 3.17, m | 69.8 | 3.17, m |
| 5''' | 77.2 | 3.28, m | 77.3 | 3.36, m | 77.3 | 3.30, m | 77.2 | 3.34, m | 77.3*[2] | 3.36, m*[4] |
| 6''' | 60.8 | 3.71, dd (11.8, 1.7), Ha; 3.47, dd (11.9, 5.9), Hb | 60.7 | 3.76, dd (11.8, 1.6), Ha; 3.49, dd (11.9, 6.1), Hb | 60.8 | 3.73, m, Ha; 3.49, dt (11.8, 5.9), Hb | 60.7 | 3.72, ddd (11.6, 5.3, 1.9), Ha; 3.47, dt (11.8, 6.0), Hb | 60.8*[3] | 3.76, ddd (11.8, 5.1, 2.0), Ha*[5]; 3.49, dt (11.9, 6.2), Hb*[6] |
| 1'''' | | | | | | | | | 102.7 | 4.58, d (7.5) |
| 2'''' | | | | | | | | | 73.3 | 3.28, m |
| 3'''' | | | | | | | | | 75.8*[1] | 3.28, m |
| 4'''' | | | | | | | | | 69.8 | 3.17, m |
| 5'''' | | | | | | | | | 77.2*[2] | 3.28, m*[4] |
| 6'''' | | | | | | | | | 60.7*[3] | 3.71, ddd (11.8, 5.2, 1.9), Ha*[5]; 3.47, dt (11.9, 6.0), Hb*[6] |
| 3'-OH | | | | | | 9.12, s | | 8.79, br s* | | |
| 4'-OH | | | | | | 9.41, br s* | | | | 9.06, br s |
| 3"-OH | | | | | | | | 8.63, br s | | 8.43, br s |
| 4"-OH | | | | | | 8.34, br s* | | 8.69, br s* | | |
| 2'''-OH | | | | | | 5.53, br s | | 5.42, br s | | 5.53, br s*[7] |
| 3'''-OH | | | | | | 5.10, d (4.3) | | 5.10, d (4.3) | | 5.11, d (4.6)*[8] |
| 4'''-OH | | | | | | 5.06, d (5.2) | | 5.06, d (5.2) | | 5.08, d (5.3)*[9] |
| 6'''-OH | | | | | | 4.66, t (5.7) | | 4.59, t (5.6) | | 4.64, t (5.9)*[10] |
| 2''''-OH | | | | | | | | | | 5.49, br s*[7] |
| 3''''-OH | | | | | | | | | | 5.08, d (5.3)*[8] |
| 4''''-OH | | | | | | | | | | 5.04, d (5.3)*[9] |
| 6''''-OH | | | | | | | | | | 4.59, t (5.8)*[10] |

$^a$Measured in DMSO-d$_6$ ($^1$H NMR for 600 MHz, $^{13}$C NMR for 150 MHz).
*Assignment may be interchanged.

TABLE 2

$^{13}$C NMR and $^1$H NMR data and attributions of compounds of formula (VII)-formula (XI).

| | formula VII | | formula VIII | | formula IX | | formula X | | formula XI | |
|---|---|---|---|---|---|---|---|---|---|---|
| No. | $\delta_C{}^a$ | $\delta_H{}^a$ | $\delta_C{}^c$ | $\delta_H{}^c$ | $\delta_C{}^a$ | $\delta_H{}^a$ | $\delta_C{}^a$ | $\delta_H{}^a$ | $\delta_C{}^b$ | $\delta_H{}^b$ |
| 1 | | 7.88, br s | | 8.25, t (5.5) | | 8.01/7.98, t (5.8) | | 8.01/7.98, t (5.8) | | |
| 2 | 36.9 | 3.18, m | 35.8 | 3.17, q (4.8) | 35.5 | 3.10, q (6.1) | 35.5 | 3.10, q (6.1) | 36.7 | 3.20, m |
| 3 | 29.5 | 1.58, quint (6.6) | 25.9 | 1.76, quint (5.8) | 26.1 | 1.68, quint (6.6) | 26.1 | 1.68, quint (6.6) | 27.5 | 1.71, quint (7.0) |
| 4 | 46.8 | 2.51, t (6.5) | 44.9 | 2.86, m | 44.6 | 2.78, m | 44.6 | 2.78, m | 46.1 | 2.58, m |
| 5 | | | | 8.47, br s | | 8.37, br s | | 8.37, br s | | |
| 6 | 48.9 | 2.46, t (6.6) | 46.6 | 2.86, m | 46.6 | 2.84, m | 46.6 | 2.84, m | 48.6 | 2.79, m |
| 7 | 26.8 | 1.35, m | 23.1 | 1.52, quint (6.4) | 23.1 | 1.52, quint (7.1) | 23.1 | 1.52, quint (7.1) | 24.6 | 1.49, m |
| 8 | 27.1 | 1.37, m | 26.3 | 1.40, quint (6.9) | 26.3 | 1.41, quint (6.9) | 26.3 | 1.41, quint (6.9) | 27.5 | 1.49, m |
| 9 | 38.4 | 3.01, q (5.8) | 37.8 | 3.03, q (5.8) | 37.8/37.6 | 3.04, q (6.1) | 37.8/37.6 | 3.04, q (6.1) | 39.3 | 3.16 t (5.9) |
| 10 | | 7.74, t (5.1) | | 7.89, t (5.4) | | 7.86/7.84, t (5.7) | | 7.86/7.84, t (5.7) | | |
| 1' | 125.1 | | 126.9 | | 136.2/136.1 | | 132.1/132.0 | | 133.4 | |
| 2' | 116.2 | 7.30, d (1.2) | 119 | 7.81, d (1.7) | 115.8 | 6.65, d (2.2) | 115.7 | 6.56, m | 117.8 | 7.04, br s |
| 3' | 146 | | 144.7 | | 146.7 | | 145 | | 146.4 | |
| 4' | 150.8 | | 147.7 | | 143.6 | | 143.3 | | 146.3 | |
| 5' | 116.8 | 6.76, d (8.3) | 115.4 | 6.77, d (8.3) | 116.9 | 6.99, d (8.2) | 115.4 | 6.61, d (8.0) | 117.1 | 6.77, s |
| 6' | 123.3 | 7.06, dd (8.3, 1.3) | 126.1 | 7.24, dd (8.4, 1.6) | 118.9 | 6.55/6.54, dd (8.3, 2.3) | 118.7 | 6.42/6.41, dd (8.0, 2.3) | 124.6 | 6.77, s |
| 7' | 139 | 7.27, d (15.5) | 137.4 | 6.52, d (13.2) | 30.6/30.5 | 2.69, t (7.4) | 30.6/30.5 | 2.63, t (7.9) | 31.8 | 2.84, t (7.1) |
| 8' | 118.3 | 6.34, d (15.7) | 120.9 | 5.80, d (12.9) | 37 | 2.32, m | 37.4/37.2 | 2.28, m | 38 | 2.51, m |
| 9' | 165.5 | | 166.6 | | 172.2/172.1 | | 172.2/172.1 | | 176.3 | |
| 1" | 132.2 | | 136.2 | | 132.1/132.0 | | 136.2/136.1 | | 133.7 | |
| 2" | 116.9 | 6.96, br s | 115.9 | 6.64, d (1.8) | 115.7 | 6.56, m | 115.8 | 6.65, d (2.2) | 116.8 | 6.63, d (2.0) |
| 3" | 145.1 | | 146.7 | | 145 | | 146.7 | | 146.1 | |
| 4" | 143.1 | | 143.7 | | 143.3 | | 143.6 | | 144.5 | |
| 5" | 115.7 | 6.68, s | 116.9 | 6.99, d (8.2) | 115.4 | 6.61, d (8.0) | 116.9 | 6.99, d (8.2) | 116.4 | 6.67, d (8.0) |
| 6" | 122.5 | 6.68, s | 119 | 6.54, dd (8.2, 1.7) | 118.7 | 6.42/6.41, dd (8.0, 2.3) | 118.9 | 6.55/6.54, dd (8.3, 2.3) | 120.8 | 6.52, dd (8.0, 2.1) |
| 7" | 30.6 | 2.67, td (8.2, 2.9) | 30.7 | 2.67, t (7.3) | 30.6/30.5 | 2.61, t (7.9) | 30.6/30.5 | 2.68, t (7.9) | 32.4 | 2.76, t (7.4) |
| 8" | 37.2 | 2.30, t (7.7) | 37.3 | 2.29, t (7.1) | 37.4/37.2 | 2.28, m | 37 | 2.32, m | 39.3 | 2.41, t (7.5) |
| 9" | 171.7 | | 171.5 | | 171.6/171.4 | | 171.6/171.4 | | 175.7 | |
| 1''' | 102.6 | 4.69, d (7.1) | 102.4 | 4.65, d (7.1) | 102.7 | 4.58, d (6.8) | 102.7 | 4.58, d (6.8) | 103.6 | 4.80, d (7.8) |
| 2''' | 73.4 | 3.29, m | 73.3*$^1$ | 3.29, m | 73.3 | 3.26, m | 73.3 | 3.26, m | 74.9 | 3.47, m |
| 3''' | 76.2*$^1$ | 3.29, m | 75.9*$^2$ | 3.29, m | 75.9 | 3.26, m | 75.9 | 3.26, m | 77.6 | 3.47, m |
| 4''' | 69.9 | 3.18, m | 69.6*$^3$ | 3.20, m | 69.9 | 3.15, m | 69.9 | 3.15, m | 71.3 | 3.38, m |
| 5''' | 77.3 | 3.33, m*$^3$ | 77.2*$^4$ | 3.29, m | 77.2 | 3.28, m | 77.2 | 3.28, m | 78.6 | 3.47, m |
| 6''' | 60.9*$^2$ | 3.76, br d (12.0), Ha*$^4$ | 60.8 | 3.75, d (11.7), Ha*$^5$ | 60.8 | 3.71, d (11.2), Ha | 60.8 | 3.71, d (11.2), Ha | 62.4 | 3.97, dd (12.0, 2.0), Ha |
| | | 3.49, dd (11.8, 5.9), Hb | | 3.48, m, Hb | | 3.47, dd (11.9, 6.0), Hb | | 3.47, dd (11.9, 6.0), Hb | | 3.72, dd (12.0, 5.8), Hb |
| 1'''' | 102.5 | 4.62, d (7.2) | 102.7 | 4.59, d (7.1) | | | | | | |
| 2'''' | 73.4 | 3.29, m | 73.4*$^1$ | 3.29, m | | | | | | |
| 3'''' | 76.0*$^1$ | 3.29, m | 76.0*$^2$ | 3.29, m | | | | | | |
| 4'''' | 69.9 | 3.18, m | 69.9*$^3$ | 3.20, m | | | | | | |
| 5'''' | 77.3 | 3.29, m*$^3$ | 77.3*$^4$ | 3.29, m | | | | | | |
| 6'''' | 60.8*$^2$ | 3.74, br d (11.2), Ha*$^4$ | 60.8 | 3.71, d (11.9), Ha*$^5$ | | | | | | |
| | | 3.49, dd (11.8, 5.9), Hb | | 3.48, m, Hb | | | | | | |
| 4'-OH | | | | 8.99, br s*$^6$ | | | | | | |
| 3"-OH | | | | 8.47, br s*$^6$ | | | | | | |

$^a$Measured in DMSO-d$_6$ ($^1$H NMR for 600 MHz, $^{13}$C NMR for 150 MHz).
$^b$Measured in CD$_3$OD ($^1$H NMR for 300 MHz, $^{13}$C NMR for 75 MHz).
$^c$Measured in DMSO-d$_6$ ($^1$H NMR for 300 MHz, $^{13}$C NMR for 75 MHz).
*Assignment may be interchanged.

TABLE 3

$^{13}C$ NMR and $^1H$ NMR data and attributions of compounds of formula (XII)
formula (XIV).

| No. | formula XII $\delta_C^b$ | formula XII $\delta_H^b$ | formula XIII $\delta_C^b$ | formula XIII $\delta_H^b$ | formula XIV $\delta_C^a$ | formula XIV $\delta_H^a$ |
|---|---|---|---|---|---|---|
| 1 | | 7.97, t (5.8) | | 8.01, t (5.8) | | 7.79, t (5.6) |
| 2 | 35.5 | 3.09, q (6.4) | 35.5 | 3.10, q (6.2) | 36.8 | 3.04, q (5.9) |
| 3 | 26 | 1.67, quint (6.8) | 26.1 | 1.68, quint (7.4) | 29.5 | 1.48, quint (6.8) |
| 4 | 44.6 | 2.76, m | 44.6 | 2.79, m | 46.9 | 2.42, t (7.0) |
| 5 | | 8.36, br s | | 8.40, br s | | |
| 6 | 46.6 | 2.82, m | 46.6 | 2.85, m | 49 | 2.41, t (7.0) |
| 7 | 23.1 | 1.50, quint (7.0) | 23.1 | 1.52, quint (7.1) | 27 | 1.30, quint (6.8) |
| 8 | 26.2 | 1.40, quint (6.9) | 26.2 | 1.41, quint (7.5) | 27.1 | 1.36, quint (6.6) |
| 9 | 37.8 | 3.04, q (6.6) | 37.8 | 3.04, q (6.1) | 38.5 | 2.99, q (6.1) |
| 10 | | 7.83, t (5.6) | | 7.86, t (5.6) | | 7.74, t (5.5) |
| 1' | 132 | | 136.2 | | 136.4 | |
| 2' | 116.8*[1] | 6.95, m | 115.8 | 6.65, d (2.2) | 116.8 | 6.55, br d (2.0) |
| 3' | 145.1 | | 146.9 | | 150.2 | |
| 4' | 144.9 | | 143.6 | | 144.5 | |
| 5' | 115.6 | 6.70, d (8.1) | 117 | 6.99, d (8.2) | 117.8 | 6.91, d (8.2) |
| 6' | 122.5 | 6.68, dd (8.2, 1.9) | 118.9 | 6.55, dd (8.2, 2.4) | 116.5 | 6.37, dd (8.2, 1.7) |
| 7' | 30.5 | 2.70, m | 30.6* | 2.69, t (7.5) | 30.9 | 2.63, m |
| 8' | 36.9 | 2.34, t (7.7) | 37 | 2.33, t (7.5) | 37.4 | 2.27, t (7.3) |
| 9' | 172.1 | | 172 | | 171.5 | |
| 1" | 132.2 | | 136.2 | | 130.4 | |
| 2" | 116.9*[1] | 6.95, m | 115.8 | 6.65, d (2.2) | 117.4 | 6.90, br s |
| 3" | 145.1 | | 146.9 | | 145.7 | |
| 4" | 144.9 | | 143.6 | | 147.3 | |
| 5" | 115.6 | 6.70, d (8.1) | 117 | 6.99, d (8.2) | 116.3 | 6.62, s |
| 6" | 122.5 | 6.68, dd (8.2, 1.9) | 118.9 | 6.55, dd (8.2, 2.4) | 122.7 | 6.62, s |
| 7" | 30.6 | 2.67, m | 30.5* | 2.68, t (7.9) | 30.6 | 2.65, m |
| 8" | 37.2 | 2.31, t (7.8) | 37.2 | 2.30, t (7.4) | 37.3 | 2.28, t (7.5) |
| 9" | 171.5 | | 171.4 | | 171.4 | |
| 1'" | 102.4 | 4.63, d (7.3)*[2] | 102.7 | 4.58, d (6.6) | 103.6 | 4.52, d (7.3) |
| 2'" | 73.3 | 3.27, m | 73.3 | 3.27, m | 73.5*[1] | 3.25, m |
| 3'" | 75.9 | 3.27, m | 75.9 | 3.27, m | 76.2 | 3.25, m |
| 4'" | 69.8 | 3.16, m | 69.9 | 3.15, m | 69.9 | 3.15, m |
| 5'" | 77.3 | 3.31, m | 77.2 | 3.27, m | 77.3 | 3.25, m |
| 6'" | 60.8 | 3.74, dd (11.8, 1.7), Ha*[3] 3.49, m, Hb | 60.8 | 3.71, d (11.2), Ha 3.47, dd (11.8, 5.9), Hb | 60.9 | 3.70, dd (11.5, 1.3), Ha*[2] 3.47, dd (12.4, 5.9), Hb*[3] |
| 1"" | 102.4 | 4.62, d (7.3)*[2] | 102.7 | 4.58, d (6.6) | 103.1 | 4.58, d (7.4) |
| 2"" | 73.3 | 3.27, m | 73.3 | 3.27, m | 73.4*[1] | 3.25, m |
| 3"" | 75.9 | 3.27, m | 75.9 | 3.27, m | 76.2 | 3.25, m |
| 4"" | 69.8 | 3.16, m | 69.9 | 3.15, m | 69.9 | 3.15, m |
| 5"" | 77.3 | 3.31, m | 77.2 | 3.27, m | 77.3 | 3.25, m |
| 6"" | 60.8 | 3.74, dd (11.9, 1.9), Ha*[3] 3.49, m Hb | 60.8 | 3.71, d (11.2), Ha 3.47, dd (11.8, 5.9), Hb | 60.9 | 3.73, dd (11.6, 1.4), Ha*[2] 3.49, dd (12.3, 5.9), Hb*[3] |

$^a$Measured in DMSO-$d_6$ ($^1H$ NMR for 600 MHz, $^{13}C$ NMR for 150 MHz).
$^b$Measured in DMSO-$d_6$ ($^1H$ NMR for 600 MHz, $^{13}C$ NMR for 100 MHz).
*Assignment may be interchanged.

Example 2 Antioxidant Activity Results of the Dicaffeoyl Spermidine Derivative Glycosides The antioxidant activity of the compounds was evaluated by using the oxygen radical absorbance capacity (ORAC) experiment. The detailed experimental procedure is as follows. 0.248 g of AAPH (2,2'-azobisisobutylamidine dihydrochloride) was added to a 50 mL phosphate buffer system to formulate a 18.3 mM AAPH stock solution. 20 μL of phosphate buffer, 20 μL solution of sample to be tested or standard substance Trolox (concentration of 6.25 μM) and 20 μL of fluorescent substance of disodium fluorescein (FL, concentration of 630 nM) were added to the wells of a 96-well plate in order. Then, 140 μL of AAPH (concentration of 18.3 mM) was quickly added to the wells of the 96-well plate, which was immediately placed in a GENios Luciferase-based microplate reader manufactured by Tecan, Switzerland, the excitation wavelength was set as 485 nm and the emission wavelength was set as 527 nm. The fluorescence intensity was measured every 2 minutes and recorded for a total of 100 min.

The antioxidant capacity of the active substance is calculated as follows: Relative ORAC value=(AUC$_{sample}$−AUC$_{blank}$)/(AUC$_{trolox}$−AUC$_{blank}$). Wherein, AUC$_{sample}$ refers to the integral area under the fluorescence decay curve of the test sample, AUC$_{trolox}$ refers to the integral area under the fluorescence decay curve of the standard substance Trolox, and AUC$_{blank}$ refers to the integral area under the fluorescence decay curve when the test sample or the standard substance Trolox is not added. The detailed results are shown in Table 4:

TABLE 4

Antioxidant activity results of dicaffolyl spermidine derivative glycosides

| compound | ORAC value (μmol TE/μmol) |
|---|---|
| formula II | 2.04 ± 0.04 |
| formula III | 1.87 ± 0.04 |
| formula IV | 1.73 ± 0.04 |

TABLE 4-continued

Antioxidant activity results of dicaffolyl spermidine derivative glycosides

| compound | ORAC value ($\mu$mol TE/$\mu$mol) |
|---|---|
| formula V | 2.96 ± 0.03 |
| formula VI | 2.71 ± 0.03 |
| formula VII | 1.02 ± 0.02 |
| formula VIII | 3.07 ± 0.02 |
| formula IX and formula X | 2.25 ± 0.02 |
| formula XI | 2.07 ± 0.03 |
| formula XII | 1.23 ± 0.04 |
| formula XIII | 2.06 ± 0.04 |
| formula XIV | 1.81 ± 0.05 |
| EGCG | 1.48 ± 0.02 |

EGCG (epigallocatechin gallate) represents a positive control drug treatment group.

The experimental results in Table 4 show that the dicaffolyl spermidine derivative glycosides of the present invention have significant antioxidant activity, wherein most of these compounds have stronger antioxidant capacity than the positive control EGCG. Therefore, the compound of the present invention can be used as an antioxidant for the prevention and treatment of the corresponding diseases.

Example 3 Test Method for the Compounds in Improving the Activity of Learning and Memory of Senile Dementia Fruit Fly (1) Cultivation of Senile Dementia Fruit Fly $W^{1118}$ (isoCJ1), as a background fruit fly of control group in the experiment, was abbreviated as "2U". The fruit flies that successfully introduced with the pathogenic A$\beta_{42}$ protein were (UAS-A$\beta_{42}$; abbreviated as "H29.3"). This strain of fruit flies was hybridized with the fruit fly expressing the Gal4 promoter in whole brain, and the fruit fly strain carrying elav-GAL4$^{c155}$ (P35) and A$\beta_{42}$ was obtained.

(2) Administration of Senile Dementia Fruit Fly

Three groups of drug-free control of healthy fruit fly, drug-free control of disease fruit fly, and dose disease fruit fly were set in the experiment.

All parents of tested fruit flies were housed and propagated at a constant temperature of 24° C. and a humidity of 42% RH (Relative humidity). On the first day after the emergence of the fruit flies, the fruit flies of control group and disease group, as well as the fruit flies to be administered were anesthetized with carbon dioxide, and then the fruit flies of the correct characters were selected into the glass tube containing food. During the dosing period, all tested fruit flies were kept in an incubator with a constant temperature of 28° C. and a constant humidity of 42% to ensure the drug taking efficiency of the fruit flies. Each day the fruit flies were administered for 4 hours, and the drug was administered from the second day after the fruit flies were selected until the 8th day.

The drugs administered were prepared on the second day after the fruit fly selection, and were administered to the fruit flies on the day of preparation. The drugs were dissolved by 100% DMSO to a concentration of 10 mM. When preparing the working solution, the 10 mM stock solution was diluted to 100 $\mu$M with 4% sucrose. In addition, the fruit flies of control group were fed sucrose water containing 1% DMSO. For each Performance Index, two tubes of fruit fly groups are required, each tube containing about 100 fruit flies.

Experiments were conducted in a light proof behavior room with constant temperature of 25° C., constant humidity of 70%. The method can be found in references[1-3].

1) During the training stage, about 100 flies were loaded into a training tube provided with a copper mesh cross electrode. Two kinds of odors of octanol (OCT) and methylcyclohexanol (MCH) were successively introduced for each 60 s with an intervals for 45 s of fresh air. 60 V pulsed electrical shock stimulation (US, pulse duration 1.5 s, interval 3.5 s) was applied to the fruit flies while introducing the 1$^{st}$ odor. No electrical shock was applied when the second odor (CS−) was introduced. Thereby one training cycle was completed.

2) In the transient memory (learning) ability test, the fruit flies that completed one training cycle were immediately transferred to the selection point of T-Maze, while CS+ and CS− were introduced from the opposite two directions. After two minutes of selection, the fruit flies on both sides were collected separately and counted after anesthesia or sacrifice. The calculation formula for the performance index (PI) is as follows: PI=[(CS−)−(CS+)]/[(CS−)+(CS+)]×100.

Using OCT and MCH as CS+ for training and testing respectively, the average of the two PIs obtained was used as PI for one experiment. PI=0 indicates that the selection of the fruit flies for the two odors in the test was 50:50, i.e., no memory was formed; PI=100 indicated that the fruit flies in the test all escaped the odor accompanying the electrical shock, i.e., perfect memory. When performing the activity test, the short-term memory deficit tests for the olfactory sensation of the non-administered healthy flies with the same genetic background (2U*H29.3), non-administered Senile dementia disease flies (P35*H29.3), and test drug administered Senile dementia disease flies were also conducted, and their total learning and memory performance indexes (PIs) was calculated respectively. The learning and memory performance index of the test drug administered Senile dementia disease flies was compared with the performance index of the non-administered healthy flies with the same genetic background (2U*H29.3), and the performance index of the non-administered Senile dementia disease flies (P35*H29.3), to evaluate effect of the test drugs against Senile dementia. The relatively higher learning and memory performance index of the test drug administered Senile dementia disease flies indicates stronger effect of the test samples against Senile dementia. One-way analysis of variance (ANOVA) was used for the comparison. As for the learning and memory performance index of the test drug administered Senile dementia disease flies and the learning and memory performance index of the non-administered (only solvent without drug sample was administered) Senile dementia disease flies, $P<0.05$ means a significant difference, $P<0.01$ means a very significant difference, $P<0.001$ means an extremely significant difference.

The data analysis and graphical display were processed by GraphPad Prism 5.01; see Table 5 for detailed results.

TABLE 5

The result for the dicaffeoyl spermidine derivative glycosides in improving the activity of learning and memory of Senile dementia fruit flies

| a | | b | | c | |
|---|---|---|---|---|---|
| Genotype/drug | PI (100 μM) | Genotype/drug | PI (100 μM) | Genotype/drug | PI (100 μM) |
| 2U*H29.3 | 51.0 ± 1.3 | 2U*H29.3 | 50.1 ± 1.0 | 2U*H29.3 | 50.2 ± 1.2 |
| P35*H29.3 | 27.2 ± 1.6# | P35*H29.3 | 22.4 ± 2.7# | P35*H29.3 | 23.3 ± 3.4# |
| Memantine | 43.1 ± 0.9*** | Memantine | 42.7 ± 0.9*** | Memantine | 44.2 ± 2.1*** |
| formula II | 35.5 ± 3.8* | formula VII | 44.6 ± 2.5*** | formula XIV | 44.6 ± 1.2*** |
| formula III | 42.9 ± 1.6*** | formula VIII | 32.2 ± 2.3* | | |
| formula IV | 42.2 ± 2.1*** | formula IX and formula X | 39.8 ± 2.4*** | | |
| formula V | 35.0 ± 1.3* | formula XI | 37.2 ± 2.9*** | | |
| formula VI | 40.2 ± 3.1*** | formula XII | 33.5 ± 3.0** | | |
| | | formula XIII | 42.5 ± 3.0*** | | |

2U*H29.3 represents a healthy fruit fly; P35*H29.3 represents a disease fruit fly; memantine represents a positive control drug treatment group. The drug treatment group was administered at a concentration of 100 μM.
Compared with 2U*H29.3 group,
P < 0.001;
compared with P35*H29.3 group,
**P < 0.01,
***P < 0.001;
n = 6, One-way analysis of variance (ANOVA).

The experimental results in Table 5 show that all the compounds of the present invention can improve the learning and memory function of Senile dementia fruit fly, and the effects of most of the compounds are superior to that of the positive control drug memantine or equivalent to that of the positive control drug.

Example 4 Anti-Respiratory Syncytial Virus (RSV) Activity Results of Dicaffeoyl Spermidine Derivative Glycosides (1) Cytotoxicity Assay 1) HEp-2 cells were seeded in 96-well cell culture plates at 100 μL/well and the cell density was 2.5×10$^5$/mL. The cells were cultured in a 37° C., 5% $CO_2$ incubator and grown into a cell single layer over about 20 h.

2) The culture fluid in the 96-well plate was discarded and the sample to be tested was half diluted into different concentrations by using maintenance solution. For each dilution, 3 replicate wells were set at 100 μL/well, and cell control wells were also set at the same time. Then they were placed in the incubator to continue the culture.

3) The cytopathic effect caused by sample toxicity was observed every day. After 72 hours, the culture solution was discarded, and according to the MTT method, 30 μL of 5 mg/mL MTT solution was added into each well. They were placed in the incubator to continue the incubation for 4 h in dark.

(2) Cytopathic Effect Assay (CPE)

1) HEp-2 cells were seeded in 96-well cell culture plates at 100 μL/well and the cell density was 2.5×10$^5$/mL. The cells were cultured in a 37° C., 5% $CO_2$ incubator and grown into a cell single layer over about 20 h.

2) The culture fluid in the 96-well plate was discarded and the sample to be tested was half diluted by using maintenance solution with the starting concentration of the monomeric compound being 50 μM, and 50 μL of sample and 50 μL of 100×TCID50 of virus dilution being added into each well. The positive control drug Ribavirin group, virus control group and cell control group were set and placed in a 37° C., 5% $CO_2$ incubator for culture.

3) The culture was continued for 60-72 hours, and the viral lesions in each group were recorded when the lesions were completely developed in the virus control group.

4) The virus-induced cytopathic effect was recorded as follows: no cellular lesion was recorded as "−", 0 to 25% cellular lesions was recorded as "+", 25% to 50% cellular lesion was recorded as "++", 50%~75% of cellular lesion was recorded as "+++", and 75% to 100% of cellular lesion was recorded as "++++". The sample concentration corresponding to the "++" lesion level is the half inhibitory concentration $IC_{50}$ of the sample against the virus.

5) Three replicates were performed independently for each experiment.

The detailed results were shown in Table 6.

TABLE 6

Anti-respiratory syncytial virus (RSV) activity results of dicaffeoyl spermidine derivative glycosides

| Compound | MNCC (μM) | $CC_{50}$ (μM) | $IC_{50}$ (μM) | SI = $CC_{50}/IC_{50}$ |
|---|---|---|---|---|
| formula II | >100 | >100 | 25 | >4 |
| formula III | >100 | >100 | 25 | >4 |
| formula IV | >100 | >100 | 25 | >4 |
| formula V | >100 | >100 | 25 | >4 |
| formula VI | >100 | >100 | 25 | >4 |
| formula VII | >100 | >100 | 50 | >2 |
| formula VIII | >100 | >100 | 50 | >2 |
| formula IX and formula X | >100 | >100 | 25 | >4 |
| formula XI | >100 | >100 | 25 | >4 |
| formula XII | >100 | >100 | 50 | >2 |
| formula XIII | >100 | >100 | 25 | >4 |
| formula XIV | >100 | >100 | 50 | >2 |
| Ribavirin | 15.32 ± 4.31 | 37.88 ± 3.82 | 2.5 | 15 |

The experimental results in Table 6 show that the compounds II-XIV of the present invention all have an anti-respiratory syncytial virus effect and are useful as antiviral agents.

The present disclosure merely illustrates some of the claimed embodiments, wherein the technical features recited in one or more technical solutions may be combined with any one or more technical solutions, and these technical solutions obtained by combination are also within the claimed scope of the present application, it is as same as these technical solutions obtained by combination have been specifically described in the present disclosure.

REFERENCES

[1] Tully T, et al. *J. Comp. Physiol. A* 1985, 157, 263-277.
[2] Tully T, et al. *Cell* 1994, 79, 35-47.
[3] Yin J C, et al. *Cell* 1994, 79, 49-58.

The invention claimed is:

1. A method of treating a neurodegenerative disease, comprising administering to a subject in need of treatment a therapeutically effective amount of dicaffeoyl spermidine derivative glycosides of formula (I) or the pharmaceutically acceptable salts thereof,

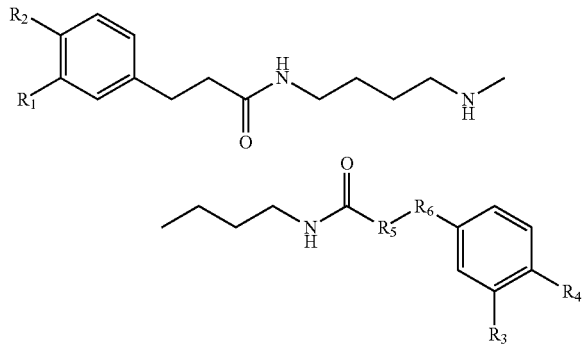

Formula (I)

wherein,
$R_1$, $R_2$, $R_3$ and $R_4$ are hydroxy, methoxy, or optionally substituted glycosyl, and at least one of $R_1$, $R_2$, $R_3$ and $R_4$ is an optionally substituted glycosyl, $R_5$ and $R_6$ are both —CH= or —CH$_2$—, wherein the optionally substituted glycosyl is optionally substituted with one or more of the following monosaccharide groups and disaccharide groups or polysaccharide groups formed by the following monosaccharides selected from the group consisting of:
glucosyl, glucuronyl, mannosyl, galactosyl, allosyl, fructosyl, sorbosyl, furanosyl, rhamnosyl, quinovosyl, arabinosyl, lyxosyl, xylosyl, ribosyl;
wherein the dicaffeoyl spermidine derivative glycosides or the pharmaceutically acceptable salts thereof further comprises pharmaceutically acceptable excipients to provide a pharmaceutical composition,
wherein the content of the dicaffeoyl spermidine derivative glycosides or the pharmaceutically acceptable salts thereof is 1% to 90% by weight of the pharmaceutical composition.

2. The method according to claim 1, wherein the neurodegenerative disease is one or more of senile dementia, Parkinson's disease, multiple sclerosis and Huntington's disease, and the senile dementia is Alzheimer's disease, vascular dementia, dementia with Lewy body or frontotemporal dementia.

3. The method according to claim 1, wherein the pharmaceutically acceptable salts are salts formed by the dicaffeoyl spermidine derivative glycosides of formula (I) with an inorganic acid or an organic acid.

4. The method according to claim 3, wherein the inorganic acid is hydrochloric acid, hydrobromic acid, sulfuric acid, or nitric acid, and the organic acid is trifluoroacetic acid, acetic acid, propionic acid, malonic acid, butyric acid, lactic acid, methanesulfonic acid, ethanesulfonic acid, benzenesulfonic acid, p-toluenesulfonic acid, maleic acid, benzoic acid, succinic acid, picric acid, tartaric acid, citric acid, or fumaric acid.

5. The method according to claim 1, wherein the compound of formula (I) is:

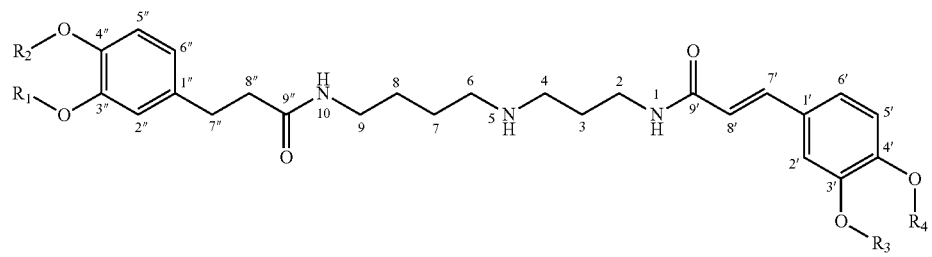

Formula (II): $R_1$ = H, $R_2$ = β-D-Glc, $R_3$ = H, $R_4$ = H
Formula (III): $R_1$ = H, $R_2$ = H, $R_3$ = β-D-Glc, $R_4$ = H
Formula (IV): $R_1$ = β-D-Glc, $R_2$ = H, $R_3$ = H, $R_4$ = H
Formula (V): $R_1$ = H, $R_2$ = H, $R_3$ = H; $R_4$ = β-D-Glc
Formula (VI): $R_1$ = H, $R_2$ = β-D-Glc, $R_3$ = β-D-Glc, $R_4$ = H
Formula (VII): $R_1$ = β-D-Glc, $R_2$ = H, $R_3$ = β-D-Glc, $R_4$ = H

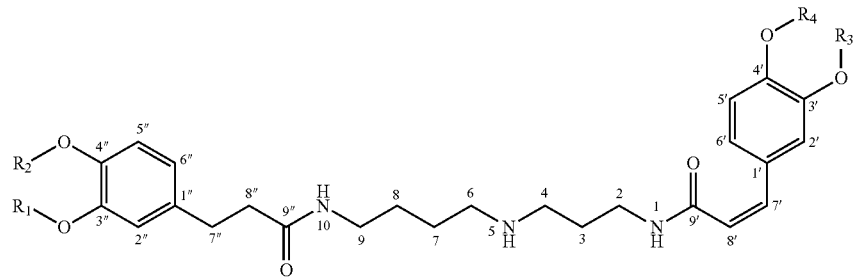

Formula (VIII): $R_1$ = H, $R_2$ = β-D-Glc, $R_3$ = β-D-Glc, $R_4$ = H

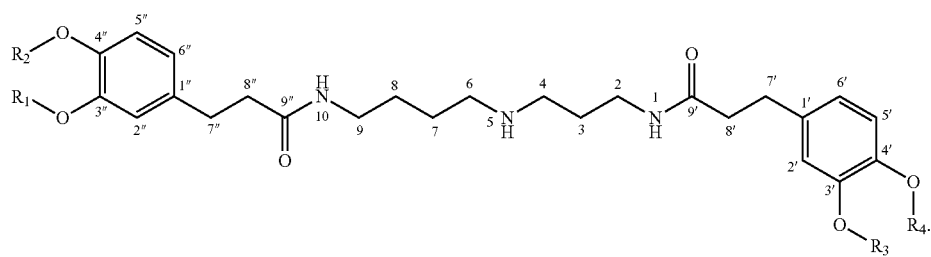
Formula (IX): $R_1 = H, R_2 = H, R_3 = H, R_4 = \beta\text{-D-Glc}$
Formula (X): $R_1 = H, R_2 = \beta\text{-D-Glc}, R_3 = H, R_4 = H$
Formula (XI): $R_1 = H, R_2 = H, R_3 = \beta\text{-D-Glc}, R_4 = H$
Formula (XII): $R_1 = \beta\text{-D-Glc}, R_2 = H, R_3 = \beta\text{-D-Glc}, R_4 = H$
Formula (XIII): $R_1 = H, R_2 = \beta\text{-D-Glc}, R_3 = H, R_4 = \beta\text{-D-Glc}$
Formula (XIV): $R_1 = \beta\text{-D-Glc}, R_2 = H, R_3 = H, R_4 = \beta\text{-D-Glc}$
\* \* \* \* \*